United States Patent
Adjei et al.

(10) Patent No.: US 6,458,338 B1
(45) Date of Patent: *Oct. 1, 2002

(54) AMINO ACID STABILIZED MEDICINAL AEROSOL FORMULATIONS

(75) Inventors: Akwete Adjei; Anthony J. Cutie, both of Bridgewater, NJ (US)

(73) Assignee: Aeropharm Technology Incorporated, Edison, NJ (US)

(*) Notice: Subject to any disclaimer, the term of this patent is extended or adjusted under 35 U.S.C. 154(b) by 21 days.

This patent is subject to a terminal disclaimer.

(21) Appl. No.: 09/617,328

(22) Filed: Jul. 17, 2000

Related U.S. Application Data

(63) Continuation-in-part of application No. 09/158,369, filed on Sep. 22, 1998, now Pat. No. 6,136,294.

(51) Int. Cl.$^7$ .................................................. A61K 9/12
(52) U.S. Cl. ........................... 424/46; 424/45; 424/489
(58) Field of Search ............................ 424/45, 46, 489

(56) References Cited

U.S. PATENT DOCUMENTS

| | | | |
|---|---|---|---|
| 2,868,691 A | 1/1959 | Porush et al. | |
| 2,885,427 A | 5/1959 | Ruh et al. | |
| 3,261,748 A | 7/1966 | Larsen | |
| 4,129,603 A | 12/1978 | Bell | |
| 4,174,295 A | 11/1979 | Bargigia et al. | |
| 5,126,123 A | 6/1992 | Johnson | |
| 5,182,097 A | 1/1993 | Byron et al. | |
| 5,190,029 A | 3/1993 | Byron et al. | |
| 5,225,183 A | 7/1993 | Purewal et al. | |
| 5,254,330 A | 10/1993 | Ganderton et al. | |
| 5,376,386 A | 12/1994 | Ganderton et al. | |
| 5,439,670 A | 8/1995 | Purewal et al. | |
| 5,474,759 A | 12/1995 | Fassberg et al. | |
| 5,492,688 A | 2/1996 | Byron et al. | |
| 5,569,450 A | 10/1996 | Duan et al. | |
| 5,594,015 A | 1/1997 | Kurtz et al. | 514/369 |
| 5,603,918 A | * 2/1997 | McNamara | |
| 5,605,674 A | 2/1997 | Purewal et al. | |
| 5,607,662 A | 3/1997 | Baskeyfield et al. | |
| 5,612,053 A | 3/1997 | Baichwal et al. | |
| 5,635,159 A | * 6/1997 | Fu et al. | |
| 5,653,962 A | 8/1997 | Akehurst et al. | |
| 5,658,549 A | 8/1997 | Akehurst et al. | |
| 5,674,471 A | 10/1997 | Akehurst et al. | |
| 5,674,472 A | 10/1997 | Akehurst et al. | |
| 5,676,929 A | 10/1997 | Akehurst et al. | |
| 5,676,931 A | * 10/1997 | Adjei et al. | |
| 5,683,676 A | 11/1997 | Akehurst et al. | |
| 5,683,677 A | 11/1997 | Purewal et al. | |
| 5,688,782 A | 11/1997 | Neale et al. | |
| 5,695,743 A | 12/1997 | Purewal et al. | |
| 5,720,940 A | 2/1998 | Purewal et al. | |
| 5,725,841 A | 3/1998 | Duan et al. | |
| 5,736,124 A | 4/1998 | Akehurst et al. | |
| 5,744,123 A | 4/1998 | Akehurst et al. | |
| 5,891,419 A | * 4/1999 | Cutie et al. | |
| 5,891,420 A | * 4/1999 | Cutie | |
| 6,129,905 A | * 10/2000 | Cutie et al. | |
| 6,136,294 A | * 10/2000 | Adjei et al. | |
| 6,193,954 B1 | 2/2001 | Adjei et al. | |

FOREIGN PATENT DOCUMENTS

| | | | |
|---|---|---|---|
| CA | 2075058 | * | 1/1991 |
| EP | 0518660 | | 12/1992 |
| GB | 2046093 | | 11/1980 |
| WO | 90/09781 | | 2/1990 |
| WO | 92/22287 | | 6/1992 |
| WO | 93/11745 | | 12/1992 |
| WO | 95/17195 | | 11/1994 |
| WO | 96/18384 | * | 6/1996 |

OTHER PUBLICATIONS

M. Jones, New Scientist, pp. 56–59, May 26, 1988.
Manufacturing Chemist, p. 3, Jun. 1988.
Organic Chemicals Department, E.I. Du Pont de Nemocers & Co., Research Disclosure, p. 70, Oct. 1977.
H.O. Spauschus, Rev. Int. Froid., vol. 11, pp. 389–392 (1988).
D.R. Strobach, Aerosol Age, pp. 32–43 (1988).
Saunders, "handbook of Aerosol Technology" $2^{nd}$ ed. pp. 30–35, 166–167, and 232–233, Von Nostrand Reinhold Co. (1979).
DuPont Update "Fluorocarbon/Ozone", published by DuPont, Willington, DE (Mar. 1987).
Dictionnarie Vidal, $55^{th}$ ed. pp. 547–548, O.V.P. Paris (1979).

* cited by examiner

*Primary Examiner*—Raj Bawa
(74) *Attorney, Agent, or Firm*—Frommer Lawrence & Haug LLP

(57) ABSTRACT

This invention relates to a medicinal aerosol formulation and more particularly, to a medicinal aerosol formulation containing a particulate drug, a propellant and a stabilizing agent selected from an amino acid, an amino acid derivative and a mixture of the foregoing.

39 Claims, No Drawings

AMINO ACID STABILIZED MEDICINAL AEROSOL FORMULATIONS

RELATED APPLICATIONS

This application is a continuation-in-part of application U.S. Ser. No. 09/158,369 filed Sep. 22, 1998, now U.S. Pat. No. 6,136,294, expressly incorporated by reference.

FIELD OF THE INVENTION

This invention relates to a medicinal aerosol formulation, and more particularly, to a medicinal aerosol formulation comprising a stabilizer selected from an amino acid, a derivative thereof or a mixture of the foregoing.

DESCRIPTION OF THE RELATED ART

Delivery of drugs to the lung by way of inhalation is an important means of treating a variety of conditions, including such common local conditions as bronchial asthma and chronic obstructive pulmonary disease and some systemic conditions including pain management, cystic fibrosis, etc. Steroids, β2 agonists, anticholinergic agents, non-steroidal antuinflammatory agents, proteins and polypeptides are among the drugs that are administered to the lung for such purposes. Such drugs are commonly administered to the lung in the form of an aerosol of particles of respirable size (less than about 10 μm in diameter). In order to assure proper particle size in the aerosol, particles can be prepared in respirable size and then incorporated into a suspension formulation containing a propellant. Alternatively, formulations can be prepared in solution form in order to avoid the concern for proper particle size in the formulation. Solution formulations must nevertheless be dispensed in a manner that produces particles or droplets of respirable size.

Once prepared an aerosol formulation is filled into an aerosol canister equipped with a metered dose valve. In the hands of the patient the formulation is dispensed via an actuator adapted to direct the dose from the valve to the patient.

It is important that an aerosol formulation be stable such that the pressurized dose discharged from the metered dose valve is reproducible. Rapid creaming, settling, or flocculation after agitation are common sources of dose irreproducibility in suspension formulations. This is especially true where a binary aerosol formulation containing only medicament and propellant, e.g. 1,1,1,2-tetrafluoroethane, is employed or where such formulation contains small amounts of surfactant as well. Sticking of the valve also can cause dose irreproducibility. In order to overcome these problems aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents, such as ethanol, have been used to overcome this problem, as described in U.S. Pat. No. 5,225,183. An alternative approach that avoids cosolvents involves materials that are soluble in hydrofluorocarbon propellants and are said to be effective surfactants or dispersing aids in an aerosol formulation. Among such materials are certain fluorinated surfactants and certain polyethyoxysurfactants.

SUMMARY OF THE INVENTION

It has surprisingly been found that novel medicinal aerosol formulations can be obtained without the use of either cosolvents, such as ethanol, or surfactants, such as sorbitan trioleate which are added to a binary aerosol formulation. Stable medicinal aerosol formulations are obtained by the use of amino acids, derivatives thereof or a mixture of the foregoing.

DETAILED DESCRIPTION OF THE INVENTION

This invention involves a stable suspension aerosol formulation suitable for pressurized delivery which comprises (1) a particulate medicament or drug or combinations of at least two medicaments or drugs, (2) a suitable propellant, and (3) a suitable stabilizer.

A suitable medicament or drug is one which is suitable for administration by inhalation, the inhalation being used for oral and nasal inhalation therapy. Therapeutic categories of drugs or medicaments include cardiovascular drugs, antiallergics, analgesics, brochodilators, antihistamines, antitussives, antifungals, antivirals, antibiotics, pain medicaments, antiinflammatories, peptides, proteins and steroids.

Particularly suitable medicaments or drugs include albuterol (also known as salbutamol), atropine, beclomethasone, esters of beclomethasone such as its monopropionate and dipropionate, budesonide, cromolyn, epinephrine, ephedrine, fentanyl, flunisolide, formoterol, ipratropium bromide, isoproterenol, pirbuterol, prednisolone, mometasone, salmeterol, amiloride, fluticasone esters, such as phosphate, monohydrate and furoate, (−)4-amino-3,5-dichloro-α-[[[6(2-pyridinyl)ethoxy]hexyl]amino]methyl]benzene-methanol. Also included are the suitable acid addition salts of the foregoing drugs, their hydrates and their other solvates. In this regard, suitable acid addition salts include the salts obtained from inorganic acids, such as hydrochloric, hydrobromic, sulfuric, nitric, phosphoric and perchloric acids as well as organic acids such as tartaric, citric, acetic, succinic, maleic, fumaric and oxalic acids. Suitable pharmaceutically acceptable solvates include solvates with ethylactate, alkanes, ethers, alcohols and water.

An preferred embodiment of this invention are aersol formulations which provide for a combination of at least two and most preferably no more than four different medicaments, such as cardiovascular drugs, antiallergenics, analgesics, bronchodilatiors, antihistamines, antitissive, antifungals, antiviral, antibiotics, pain medicaments, antinflammatories, peptides, proteins and steroids as well as the use of these aerosol formulations to treat the disease states associated with these medicaments. These medicaments and their use to treat a particular disease state are well known to practitioners of the art.

This invention includes the derivatives of the foregoing medicaments. These derivatives include all the salt, ester, solvate and hydrate forms of the foregoing drugs as well as their geometric and optical isomers, including their chiral forms. Such derivatives are well known to a practitioner in this art.

Especially preferred, are formulations which comprise combinations comprising at least two different medicants, such as β2-adrenergic agonists, corticosteroids, anticholinergics and leucotriene modulators. Especially preferred are β2-adrenergic agonists, such as albuterol and formoterol, and corticosteroids, such as mometasone, hydrocortisone, fludrocortisone, dexamethasone, predniscone, cortisone, aldosterone hemi-acetal, betametasone, beclomethasone dipropionate, triamcinolone acetonide, budesonide dipropionate, fluticasone propionate and fluniscolide, anticholinergics such as ipratopium bromide, histamine antagonists (mast cell modulators). Such as cromolyn, and non-steroidal antiinflammatory agents, such as acetominophen or ibuprofen.

The leucotrienes contemplated in this invention are those which implicated as mediators of allergic and inflammatory responses associated with bronchial asthma and rheumatoid arthritis, these medicaments are known in the art to constrict dramatically the pulmonary airways and small blood vessels. Thus, inhibitors or antagonists of leucotrienes are effective mediators of the allergic responses typified by asthma and may be used to treat bronchial asthma and other diseases state associated with inflammation of the airways.

The leucotriene modulators contemplated in this application include, but not limited, to the following:

1. Inhibitors or antagonists of lecotriene, including the PAF receptor antagonists and 5-lipoxynase inhibitors, for example 2,5-diaryl tetrahydrofurans, 2,5-diaryl tetrahydrothiophenes, 2,4-diaryl tetrahydrofurans, 2,4-diaryl tetrahydrothiophenes, 1,3-diaryl cyclopentanes, 2,4-diaryl pyrrolidines, and 2,5-diaryl pyrrolidines, triazolo(4,3-A)(1, 4)benzodiazepines and thieno(3,2-F)(1,2,4)triazolo(4,3-A) (1,4)diazepine compounds, 6-phenyl-4H-s-triazolo[4,3-a][1, 4]benzodiazepines (see, U.S. Pat. Nos. 5,856,323; 5,358, 938; 4,959,361; and 3,987,052), including, both optically pure and racemates (U.S. Pat. No. 5,629,337). An example of this group of compounds is Zileuton® (Abbott Laboratories) and Acolate® (Merck).

2. Chromone-2-carboxylic acid derivatives as antagonists of SRS-A (slow reacting substance of anaphylaxis (see, Samuelsson et al., Department of Chemistry, Karolinska Institutet, Stockholm, Sweden, TIPS, 227, May, 1980; J. Med. Chem. 20 371 (1977)), such as 7-[3-(4-acetyl-3-hydroxy-2-propylphenoxy)-2-hydroxypropoxy]-4-oxo-8-propyl-4H-1-benzopyran-2-carboxylate (FPL 55712), which is a specific antagonist of SRS-A as well as a standard for evaluating other inhibitors;

3. Aryloxyalkyloxy- and aralkyloxy-4-hydroxy-3-nitrocoumarins as antagonists of SRS-A and inhibitors of histamine release, (see, e.g. Buckle et al., J. Med. Chem. 22 158 (1979); U.S. Pat. No. 4,296,237; European Patent No. 0036663; U.S. Pat. No. 4,296,120; and U.S. Pat. No. 4,296, 129), as well as other compounds which act as inhibitors of SRS-A including oxiranbutyric acid esters, 3-hydroxy-4-substituted-3-pyrroline-2,5-diones or carboxy-oxo-pyrrolidino)phenyl alkenamides and esters or (carboxyacylamino)phenyl alkenamides and esters, or the substituted derivatives of these before mentioned compounds, including, but not limited, to alkyl, hydroxy amino, dialkylamino, hydroxymethyl, aminomethyl, alkylaminomethyl or alkanoylaminomethyl of 1 to 12 carbon atoms; —CN, —CONH$_2$ or —CO$_2$M in which M is hydrogen, aryl, phenyl, or naphthyl, cyclohexyl, cyclopentyl, or fluoromethoxy; or 4. Antagonists and inhibitors of leukotrienes including N-o-tolylsulfonylbenzamide compounds.

All of the aforemention mentioned prior literature is expressly incorporated by reference. These medicaments are known in the art to treat inflammatory diseases and include medicaments that block release, production, secretion, or any other biochemical action of arachidonic acid, prostaglandines, thromxanes, or other leukotrienes that participate in inflammatory rections, exhibit chemotactic activities, stimulate lysosomal enzyme releases and act as important factors in the immediate hypersensitivity reaction.

Especially preferred medicaments include groups comprising [1-formyl-5-(cyclopentyloxycarbonyl)amino-1H-indol-3-ylmethyl]-3-methoxy-N-o-tolylsulfonylbenzamide, [1-(hydroxycarbamoyl)-5-(cyclopentyloxycarbonyl)amino-1H-indol-3-ylmethyl]-3-methoxy-N-o-tolylsulfonyl-benzamide, [1-((2-carboxyethyl)carbamoyl)-5-(cyclopentyloxycarbonyl)amino-1H-indol-3-ylmethyl]-3-methoxy-N-o-tolylsulfonylbenzamide, [1-((2-tetrazolylethyl)carbamoyl)-5-(cyclopentyloxycarbonyl) amino-1H-indol -3-ylmethyl]3-methoxy-N-o-tolylsulfonylbenzamide, [1-(methylphenylcarbamoyl)-5-(cyclopentyloxycarbonyl)amino-1H-indol-3-ylmethyl]-3-methoxy-N-o-tolylsulfonylbenzamide, [1-(diphenylcarbamoyl)-5-(cyclopentyloxycarbonyl)amino-1H-indol-3-ylmethyl]-3-methoxy-N-o-tolylsulfonyl-benzamide; [1-carbamoyl-5-(cyclopentyloxycarbonyl) amino-1H-indol-3-ylmethyl]-3-methoxy-N-o-tolylsulfonylbenzamide, and [1-(pyrrolidine-carbonyl)-5-(cyclopentyloxycarbonyl)amino-1H-indol3-ylmethyl]-3-methoxy-N-o-tolylsulfonylbenzamide. Also, included are the pharmaceutically acceptable salts of these agents, including addition salts derived from organic or inorganic acids such as hydrochloric, hydrobromic, sulfuric, phosphoric, methane sulfonic, nitric, p-toluene sulfonic, acetic, citric, maleic, succinic acid, and the like. In addition, the compounds in their free carboxylic acid form may be converted by standard techniques well-known to the practitioner to their corresponding alkali metal (e.g. sodium or potassium), alkaline earth metal (e.g. calcium or magnesium), ammonium or primary, secondary and tertiary alkylamine salts, the latter containing from 1 to 6 carbon atoms in their alkyl moieties or a pharmaceutically acceptable salt thereof. These components are known in the literature and are described, for example in Brown et al., J. Med. Chem., vol. 35(13), pp. 2419 to 2439 (1992); Jacobs et al., J. Med. Chem., vol. 37(9), pp. 1282 to 1297 (1994); AU000646587 Australia 3/1993; McFadden, E. R., Jr., Am. Rev. Resp. Dis., vol. 147 pp. 1306–1310 (1993); Greenberger, P. A., Chest, vol. 101 pp. 418S–421S (1992); Lipworth, B. J., Pharmacol. Ther., vol. 58 pp. 173–209 (1993); Busse, W. W., Chest, vol. 104 pp. 1565–1571 (1993); Anonymous; Executive Summary: Guidelines for the Diagnosis and Management of Asthma, Public Health Service, Publication 91–3042A, NIH, Bethesda, MD., pp. 1–44 (1991); Israel, E., and Drazen, J. M., N. Engl. J. Med., vol., 331 pp. 737–739 (1994); or Barnes, P. J., N. Engl. Med., vol. 332 pp. 868–875 (1995). All these prior publications are expressly incorporated by reference.

For purposes of the formulations of this invention, which are intended for inhalation into the lungs, the medicament or drug is preferably micronized whereby a therapeutically effective amount or fraction (e.g., ninety percent or more) of the drug is particulate. Typically, the particles have a diameter of less than about 10 microns, and preferably less than about 5 microns, in order that the particles can be inhaled into the respiratory tract and/or lungs.

The particulate medicament or drug is present in the inventive formulations in a therapeutically effective amount, that is, an amount such that the drug can be administered as an aerosol, such as topically, or via oral or nasal inhalation, and cause its desired therapeutic effect, typically preferred with one dose, or through several doses. The particulate drug is administered as an aerosol from a conventional valve, e.g., a metered dose valve.

The term "amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.005 parts by weight to about 2 parts by weight based on 100 parts by weight of the propellant.

A suitable propellant is selected. A suitable propellant is any fluorocarbon, e.g. a 1–4 hydrogen containing flurocarbon(, such as $CHF_2CHF_2$, $CF_3CH_2F$, $CH_2F_2CH_3$ and $CF_3CHFCF_3$)), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as mixtures of propellants 11, 12 and 114. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of drug from an aerosol canister.

A suitable stabilizer is selected. A suitable stabilizer includes (1) an amino acid selected from (a) a monoamino carboxylic acid of the formula, $H_2N$—R—COOH (I), (b) a monoamino dicarboxylic acid of the formula, $H_2N$—R $(COOH)_2$ (II) and (c) a diamino monocarboxylic acid of the formula $(H_2N)_2$—R COOH (III), where R is a straight or branched alkyl radical of from 1 to 22 carbon atoms, which can be mono or poly-substituted with moieties such as sulfide (—S—), oxide (—O—), hydroxyl (—OH), amide (—NH), sulfate (—SO4); aryl of the formula

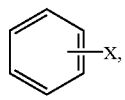

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizoyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, (c) esters of the carboxylic acid group obtained from aliphatic straight or branched chain alcohols of from 1 to 6 carbon atoms, e.g. L-aspartyl-L-phenylalanine methylester (Aspartame®), and (3) a mixture of the amino acid and the derivative of the amino acid.

Suitable amino acids of the formula I include glycin, glycine, alanine, valine, leucine, isoleucine, methionine, threonine, isovaline, phenylalanine, tyrosine, serine, cysteine, N-acetyl-L-cysteine, histidine, tryptophan, pro line, and hydroxyproline, e.g. trans-4-hydroxy proline. Compounds of the formula II include, aspartic acid, and glutamic acid, compounds of the formula (III) include arginine, lysine, hydroxylysine, ornithine, asparagine, and citrulline.

An aerosol formulation preferably comprises the stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about two or three seconds after agitation. The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.000002 percent by weight, to about 20% by weight, more preferably about 0.0002 percent to about 10% by weight, based on the weight of the formulation.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

Generally the formulations of the invention can be prepared by combining (i) the drug in an amount sufficient to provide a plurality of therapeutically effective doses; (ii) the stabilizer in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

What is claimed is:

1. A non-aqueous medicinal aerosol formulation, which consists essentially of:
   (a) a therapeutically effective amount of a combination of at least two different particulate medicaments selected from the group consisting of β-2 adrenergic agonists, corticosteroids, anticholinergics, histamine antagonists, non-steroidal antiinflammatory agents and leucotriene modulators;
   (b) a propellant; and
   (c) a stabilizer selected from an amino acid, an analogue thereof, or a mixture of the foregoing.

2. The formulation as defined in claim 1 wherein said stabilizer is selected from the group consisting of glycine, alanine, valine, leucine, isoleucine, methionine, threonine, isovaline, phenylalanine, tyrosine, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

3. The formulation as defined in claim 1 wherein the β2 adrenergic agonists are albuterol, formoterol or the pharmaceutically acceptable salts, esters, hydrates, solvates or geometric or optical isomers of the foregoing.

4. The formulation as defined in claim 1 wherein the corticosteroides are selected from the group consisting of mometasone, hydrocortisone, fludrocortisone, dexamethasone, prednisone, cortisone, aldosterone hemiacetal, betametasone, beclomethasone dipropionate, triamcinolone acetonide, budesonide dipropionate, fluticasone propionate, fluniscolide, the pharmaceutically acceptable salts, esters, hydrates, solvates and geometric or optical isomers of the foregoing and a mixture of any of the foregoing medicaments used.

5. The formulation as defined in claim 1 where the anticholinergic agent is cromolyn and the antiinflammatory agent is acetominophen or ibuprofen.

6. The formulation as defined in claim 1 wherein the leucotriene modulator is selected from the group consisting of [[1-formyl-5-(cyclopentyloxycarbonyl)amino-1H-indol-3-ylmethyl]-3-methoxy-N-o-tolylsulfonylbenzamide, [1-(hydroxycarbamoyl)-5-(cyclopentyloxycarbonyl)amino-1H-indol-3-ylmethyl]-3-methoxy-N-o-tolylsulfonylbenzamide, [1-((2-carboxyethyl)carbamoyl)-5-(cyclopentyloxycarbonyl)amino-1H-indol-3-ylmethyl]-3-methoxy-N-o-tolylsulfonylbenzamide; [1-((2-tetrazolylethyl)carbamoyl)-5-(cyclopentyloxycarbonyl)amino-1H-indol-3-ylmethyl]-3-methoxy-N-o-tolylsulfonylbenzamide; [(1-(methylphenylcarbamoyl)-5-(cyclopentyloxycarbonyl)amino-1H-indol-3-ylmethyl]-3-methoxy-N-o-tolylsulfonylbenzamide; [1-(diphenylcarbamoyl)-5-(cyclopentyloxycarbonyl)amino-1H-indol-3-ylmethyl]-3-methoxy-N-o-tolylsulfonylbenzamide; [1-carbamoyl-5-(cyclopentyloxycarbonyl)amino-1H-indol-3-ylmethyl]-3-methoxy-N-o-tolylsulfonylbenzamide; and [1-(pyrrolidine-carbonyl)-5-(cyclopentyloxycarbonyl)amino-1H-indol-3-ylmethyl]-3-methoxy-N-o-tolylsulfonylbenzamide, the pharmaceutically acceptable salts of the forgoing, and a mixture of any of the foregoing medicaments.

7. The formulation as defined in claim 1, wherein combination comprises of a corticosteroid and β2-adrenergic agonist.

8. The formulation as defined in claim 1, wherein the combination comprises a corticosteroid and an anticholinergic agent.

9. The formulation as defined in claim 1, wherein the combination comprises of a corticosteroid and a leucotriene modulator.

10. The formulation as defined in claim 1, wherein the combination comprises of a corticosteroid, a β-2 adrenergic agonist and a leucotriene modulator.

11. The formulation as defined in claim 7, wherein the corticosteroid is fluticasone or fluticasone proprionate.

12. The formulation as defined in claim 1 wherein the combination comprises a β-2 adrenergic agonist and a leucotriene modulator or a β-2 adrenergic agonist and a anticholinergic.

13. The formulation as defined in claim 1, wherein the combination comprises a histamine antagonist or an antiinflammatory agent.

14. The formulation as defined in claim 1, wherein said propellant is selected from the group consisting of 1,1,1,2-tetrafluoroethane, 1,1,1,2,3,3,3-heptafluoropropane or a mixture thereof.

15. A method of preparing a medicinal aerosol formulation according to claim 1, which comprises:
   (a) combining (i) said combination of medicaments in an amount sufficient to provide a plurality of therapeutically effective doses, (ii) said propellant in an amount sufficient to propel a plurality of said therapeutically effective doses from an aerosol canister; and (iii) said stabilizer in an amount effective to stabilize the formulation; and
   (b) dispersing components (i), (ii) and (iii).

16. A metered dose inhaler containing a non-aqueous medicinal aerosol formulation, the formulation consisting essentially of:
   (a) a combination of at least two different drugs in particulate form in a therapeutically effective amount which are selected from the group consisting of selected from the group consisting of β-2 adrenergic agonists, corticosteroids, anticholinergics, histamine antagonists, non-steroidal antiinflammatory agents and leucotriene modulators;
   (b) a propellant; and
   (c) a stabilizer selected from an amino acid, an amino acid analogue, or a mixture of the foregoing, present in an amount sufficient to stabilize the formulation to prevent settling, creaming or flocculation for a time sufficient to allow reproducible dosing of the drug after agitation of the formulation.

17. The metered dose inhaler as defined in claim 16 wherein the stabilizer is selected from the group consisting of glycin, glycine, alanine, valine, leucine, isoleucine, methionine, threonine, isovaline, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

18. The metered dose inhaler as defined in claim 16 wherein said stabilizer is present in an amount of 0.000002% by weight to about 20% by weight based on the weight of the medicinal aerosol formulation.

19. The metered dose inhaler as defined in claim 16, wherein the medicaments for the combination are selected from the group consisting of β-2 adrenergic agonists, corticosteroids, anticholorergics, and leucotriene modulators.

20. The metered dose inhaler as defined in claim 16, wherein the propellant is selected from the group consisting of 1,1,1,2-tetrafluoroethane, 1,1,1,2,3,3,3-heptafluoropropane and a mixture thereof.

21. A method of treating in a patient a condition of treatment by oral or nasal inhalation which comprises administering a formulation according to claim 1 to said patient by oral or nasal inhalation.

22. A non-aqueous medicinal aerosol formulation, which consists essentially of:
    (a) a therapeutically effective amount of a combination of at least two different particulate medicaments selected from the group consisting of corticosteroids, anticholinergics, histamine antagonists, non-steroidal antiinflammatory agents and leucotriene modulators;
    (b) a propellant;
    (c) a stabilizer selected from an amino acid, a analogue thereof, or a mixture of the foregoing; and
    (d) a cosolvent wherein the propellant and solvent are different compounds.

23. The formulation as defined in claim 22 wherein said stabilizer is selected from the group consisting of glycine, alanine, valine, leucine, isoleucine, methionine, threonine, isovaline, phenylalanine, tyrosine, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

24. The formulation as defined in claim 22 wherein the corticosteroides are selected from the group consisting of mometasone, hydrocortisone, fludrocortisone, dexamethasone, prednisone, cortisone, aldosterone hemiacetal, betametasone, beclomethasone dipropionate, triamcinolone acetonide, budesonide dipropionate, fluticasone propionate, fluniscolide, the pharmaceutically acceptable salts, esters, hydrates, solvates and geometric or optical isomers of the foregoing and a mixture of any of the foregoing medicaments are used.

25. The formulation as defined in claim 22 where the anticholinergic agent is cromolyn and the antiinflammatory agent is acetominophen or ibuprofen.

26. The formulation as defined in claim 22 wherein the leucotriene modulator is selected from the group consisting of [[1-formyl-5-(cyclopentyloxycarbonyl)amino-1H-indol-3-ylmethyl]-3-methoxy-N-o-tolylsulfonylbenzamide, [1-(hydroxycarbamoyl)-5-(cyclopentyloxycarbonyl)amino-1H-indol-3-ylmethyl]-3-methoxy-N-o-tolylsulfonylbenzamide, [1-((2-carboxyethyl)carbamoyl)-5-(cyclopentyloxycarbonyl)amino-1H-indol-3-ylmethyl]-3-methoxy-N-o-tolylsulfonylbenzamide; [1-((2-tetrazolylethyl)carbamoyl)-5-(cyclopentyloxycarbonyl)amino-1H-indol-3-ylmethyl]-3-methoxy-N-o-tolylsulfonylbenzamide; [1-(methylphenylcarbamoyl)-5-(cyclopentyloxycarbonyl)amino-1H-indol-3-ylmethyl]-3-methoxy-N-o-tolylsulfonylbenzamide; [I -(diphenylcarbamoyl)-5-(cyclopentyloxycarbonyl)amino-1H-indol-3-ylmethyl]-3-methoxy-N-o-tolylsulfonylbenzamide; [1-carbamoyl-5-(cyclopentyloxycarbonyl)amino-1H-indol-3-ylmethyl]-3-methoxy-N-o-tolylsulfonylbenzamide; and [1-(pyrrolidine-carbonyl)-5-(cyclopentyloxycarbonyl)amino-1H-indol-3-ylmethyl]-3-methoxy-N-o-tolylsulfonylbenzamide, the pharmaceutically acceptable salts of the forgoing, and a mixture of any of the foregoing medicaments.

27. The formulation as defined in claim 22, wherein the combination comprises a corticosteroid and an anticholinergic agent.

28. The formulation as defined in claim 22, wherein the combination comprises of a corticosteroid and a leucotriene modulator.

29. The formulation as defined in claim 22, wherein the combination comprises a histamine antagonist or an anti-inflammatory agent.

30. The formulation as defined in claim 22, wherein said propellant is selected from the group consisting of 1,1,1,2-tetrafluoroethane, 1,1,1,2,3,3,3-heptafluoropropane and a mixture thereof.

31. The formulation as defined in claim 22, which includes a cosolvent.

32. The formulation as defined in claim 31, wherein the cosolvent is ethanol.

33. A method of preparing a medicinal aerosol formulation according to claim 22, which comprises:
    (a) combining (i) said combination of medicaments and cosolvent, in an amount sufficient to provide a plurality of therapeutically effective doses, (ii) said propellant in an amount sufficient to propel a plurality of said therapeutically effective doses from an aerosol canister; and (iii) said stabilizer in an amount effective to stabilize the formulation; and
    (b) dispersing components (i), (ii) and (iii).

34. A metered dose inhaler containing the non-aqueous medicinal aerosol formulation according to claim 22.

35. The metered dose inhaler as defined in claim 34 wherein the stabilizer is selected from the group consisting of glycine, alanine, valine, leucine, isoleucine, methionine, threonine, isovaline, serine, histidine, tryptophan, proline, hydroxyproline, arginine, ornithine, asparagine, citrulline, aspartic acid, cysteine, glutamic acid, glutamine, lysine, hydroxylysine, N-acetyl-L-cysteine, phenylalanine, trans-4-hydroxy-L-proline, tyrosine, L-aspartyl-L-phenylalanine methylester and a mixture of any of the foregoing.

36. The metered dose inhaler as defined in claim 34 wherein said stabilizer is present in an amount of 0.000002% by weight to about 20% by weight based on the weight of the medicinal aerosol formulation.

37. The metered dose inhaler as defined in claim 34, wherein the propellant is selected from the group consisting of 1,1,1,2-tetrafluoroethane, 1,1,1,2,3,3,3-heptafluoropropane and a mixture thereof.

38. The metered dose inhaler as defined in claim 34, wherein the cosolvent is ethanol.

39. A method of treating in a patient a condition of treatment by oral or nasal inhalation which comprises administering a formulation according to claim 22 to said patient by oral or nasal inhalation.

* * * * *